United States Patent [19]

Kessous-Elbaz et al.

[11] Patent Number: 5,569,827
[45] Date of Patent: Oct. 29, 1996

[54] TRANSGENIC MOUSE FOR THE NEURONAL EXPRESSION OF HIV GP160

[75] Inventors: Allégria Kessous-Elbaz, Côte St-Luc; Jean Michaud; Fouad Berrada, both of Montréal, all of Canada

[73] Assignee: Universite de Montreal, Montreal, Canada

[21] Appl. No.: 254,395

[22] Filed: Jun. 6, 1994

[51] Int. Cl.$^6$ ............................ C12N 15/00; C07H 21/02
[52] U.S. Cl. ........................ 800/2; 435/122.3; 536/23.1; 800/DIG. 1; 800/DIG. 4
[58] Field of Search ....................................... 800/2

[56] References Cited

PUBLICATIONS

Pullian et al AIDS Res & Human Retro 9(5):439, 1993.
Toggas et al Nature 367: 188, 1994.
Julien et al Genes & Develop 1: 1085, 1982.
Freed et al J of Virol 63(11): 4670, 1989.
Brenneman, D. E. et al., 1988, Nature (London), 335:639–642.
Budka, H., 1990 a), In: Chopra J, Jagannathan K, Sawhney IMS (eds) Advances in Neurology. Excerpta Medica, Amsterdam, 193–202.
Budka, H., 1990 b), Acta Neuropathol., 79:611–619.
Budka, H. et al., 1991; Brain Patholo., 1:143–152.
Cheng–Mayer, C. et al., 1987, Proc. Natl. Acad. Sci. USA, 84:3526–3530.
Dreyer, E. B. et al., 1990, Science, 248:364–367.
Epstein, L. G. et al., 1993, Ann. Neurol., 33:429–436.
Epstein, L. G. et al., 1986, Pediatrics, 78:678–687.
Guy, C. T. et al., 1992, Mol. Cell. Biol., 12:954–961.
Gyorkey, F. et al., 1987, J. Infect. Diseases, 155:870–876.
Janssen, R. S., 1991, Neurology, 41:778–785.
Julien, J. P. et al., 1987, Genes & Development, 1:1085–1095.
Ketzler, S. et al., 1990, Acta Neuropathol. (Berl), 80:92–94.
Koenig, S. et al., 1986, Science, 233:1089–1093.
Lee, M. R. et al., 1987, Science, 237:1047–1051.
Levy, J. A. et al., 1985, Lancet, ii:586–588.
Lipton, S., 1991, Brain Pathology, 1:193–199.
Lipton, S. A., 1992, Trends Neurosci., 15: 75–79.
Masliah, E. et al., 1992, Lab. Investigation, 66:285–291.
Navia, B. A. et al., 1986 b), Ann. Neurol., 19:525–535.
Navia, B. A. et al., 1986 a), Ann. Neurol., 19:517–524.
Price, R. W. et al., 1988, Science, 239:586–592.
Pulliam, L. et al., 1993, AIDS Res Hum Retroviruses, 9:439–444.
Savio, T. et al., 1993, J. Neurosc. Res., 34:265–272.
Shen, Y. M. et al., 1982, Mol. Cell. Biol., 2:1145–1154.
Stein, B. S. et al., 1990, J Biol Chem, 265:2640–2649.
Stoler, M. H. et al., 1986, JAMA, 256:2360–2364.
Sweetnam, P. M. et al., 1993, Eur. J. Neurosc., 5:276–283.
Toggas, S. M. et al., 1994, Nature, 367:188–193.
Vazeux, R. et al., 1987, American J. Pathol., 126:403–410.
Villa, G. et al., 1993, J Neur Neurosurgery Psy, 56:878–884.
Weis, S. et al., 1993, Acta Neuropathol, 85:185–189.
Wigdahl, B. et al., 1989, AIDS Res. Hum. Retroviruses, 5:369–374.
Wiley, C. A. et al., 1986, Proc. Natl. Acad. Sci. USA, 83:7089–7093.

Primary Examiner—Suzanne E. Ziska
Attorney, Agent, or Firm—Kevin M. Farrell

[57] ABSTRACT

The present invention relates to a transgenic non-human mammal, whose germ cells and somatic cells contain a recombinant env gene sequence which is operably linked to a promoter effective for the expression of the gene in the neuronal tissues of the mammal and effective for the simulation of neurological syndromes associated with HIV-1, the gene being introduced into the mammal, or an ancestor of the mammal, at an embryonic stage. The transgenic non-human mammal is such that transcription of the env gene may be under the control of a promoter sequence, such as a neuron specific promoter of human neurofilament light gene (NFL). The promoter can be synthetic or inducible. The transgenic non-human mammal can be a rodent, such as a mouse.

1 Claim, 7 Drawing Sheets

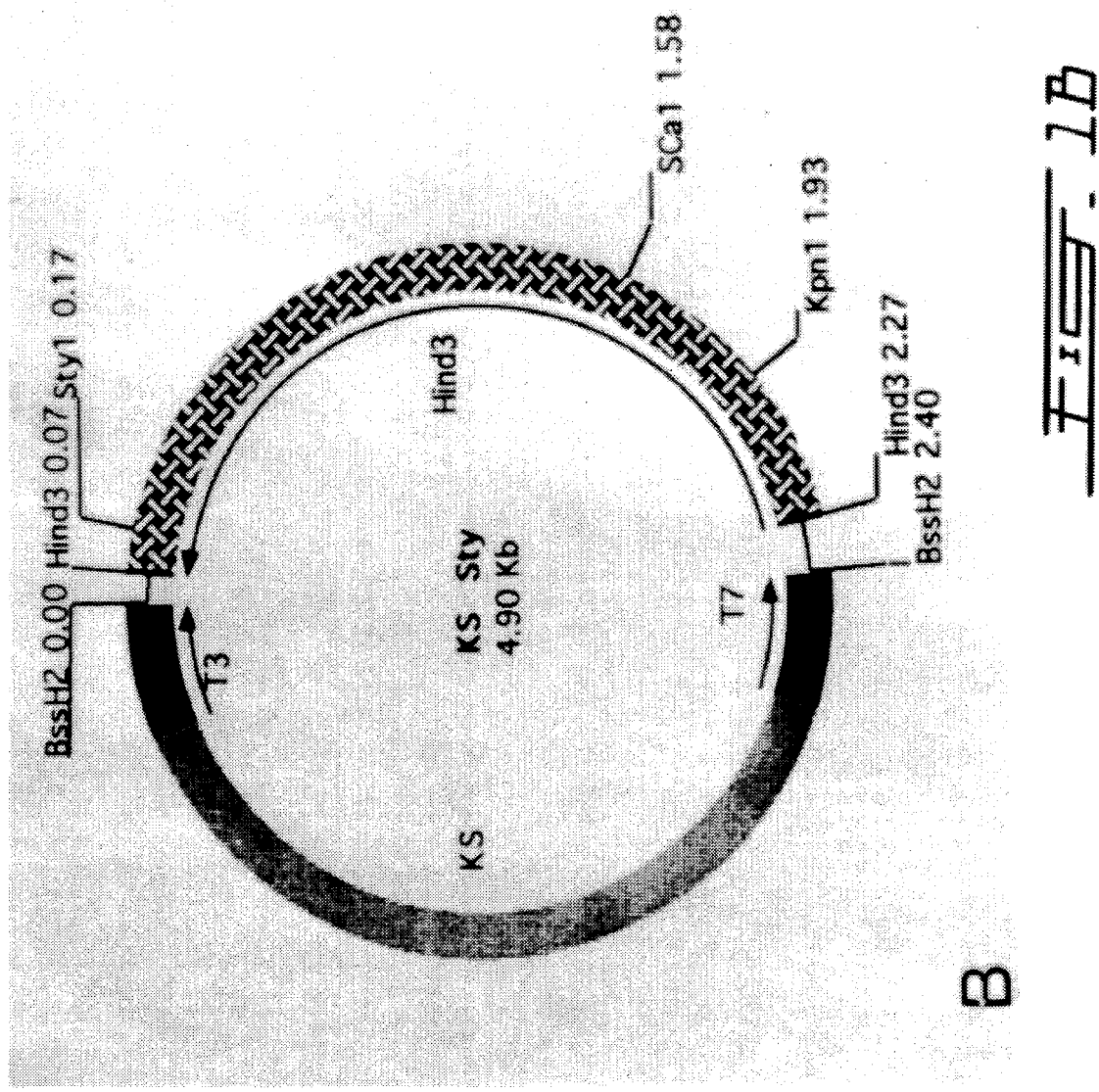

TRANSGENIC MOUSE FOR THE NEURONAL EXPRESSION OF HIV GP160

BACKGROUND OF THE INVENTION (a) Field of the Invention

The invention relates to a transgenic animal for the neuronal expression of HIV-1 gp160.

(b) Description of Prior Art

Human immunodeficiency virus type 1 (HIV-1) is the causative agent of the acquired immune deficiency syndrome (AIDS). As a member of the lentivirinae subfamily of retroviruses, it is recognized for its ability to target the immune system and the nervous tissue (Navia, B. A. et al., 1986 b), *Ann. Neurol.*, 19:525–535; Navia, B. A. et al., 1986 a), *Ann. Neurol.*, 19:517–524).

A few weeks after the primary infection with HIV-1, a burst of virus replication with a high level of viremia occurs, it is during that phase of infection that the virus likely reaches the central nervous system (CNS) (Price, R. W. et al., 1988, *Science*, 239:586–592). In most cases it remains clinically silent for highly variable periods of time. Occasionally, it produces an acute meningitis or meningoencephalitis. However, in a large number of AIDS patients (30–40%) the virus entry in the CNS intiates a slowly progressive dementing syndrome termed HIV-1-associated motor/cognitive complex (Janssen, R. S., 1991, *Neurology*, 778:773–785), which impairs cognitive and motor functions and induces behavorial disorders. At autopsy, up to 96% of these patients show neuropathological changes (Budka, H., 1990a), In: *Chopra J, Jagannathan K, Sawhney IMS (eds) Advancesin Neurology. Excerpta Medica, Amsterdam,* 193–202; price, R. W. et al., 1988, *Science*, 239:586–592; Weis, S. et al., 1993, *Acta Neuropathol,* 85:185–189) that typically define the HIV-1 encephalopathy (HIVE) or leukoencephalopathy (HIVL) (Villa, G. et al., 1993, *J Neur Neurosurgery Psy*, 56:878–884; (Weis, S. et al., 1993, *Acta Neuropathol,* 85:185–189).

HIVE is mainly characterized by brain atrophy and histological changes that include white matter pallor and multiple loosely delimitated inflammatory foci disseminated in the gray and white matter (Navia, B. A. et al., 1986 a), *Ann. Neurol.*, 19:517–524; Weis, S. et al., 1993, *Acta Neuropathol*, 85: 185–189). These foci are composed of microglial cells, a few lymphocytes, reactive astrocytes and very charasteristic multinucleated cells of monocyte/macrophages origin (Budka, H., 1990 a), In: *Chopra J, Jagannathan K, Sawhney IMS (eds) Advances in Neurology. Excerpta Medica, Amsterdam,* 193–202; Budka, H., 1990 b), *Acta Neuropathol.,* 79:611–619; Budka, H. et al., 1991, *Brain Patholo.,* 1:143–152). HIVL is characterized by diffuse myelin loss, gliosis and perivascular infiltration by monocytes and more rarely multinucleated microglia/macrophages. The deep white matter is preferentially and symmetrically affected (Budka, H., 1990 a), In: *Chopra J, Jagannathan K, Sawhney IMS (eds) Advances in Neurology. Excerpta Medica, Amsterdam,* 193–202; Budka, H., 1990 b), *Acta Neuropathol.,* 79:611–619; Budka, H. et al., 1991, *Brain Patholo.,* 1:143–152). In HIVE as well as in HIVL, the giant multinucleated cells are considered as the pathological hallmark and in both, morphometric studies have clearly demonstrated a significant neuronal loss (Epstein, L. G. et al., 1986, *Pediatrics,* 78:678–687; Ketzler, S. et al., 1990, *Acta Neuropathol.* (Berl), 80:92–94; Masliah, E. et al., 1992, *Lab. Investigation,* 66:285–291; Weis, S. et al., 1993, *Acta Neuropathol,* 85:185–189). In addition to these CNS changes, the spinal cord of HIV-1 infected patients may also present alterations such as myelitis or a peculiar vacuolar myelopathy for which no clear etiology has been determined yet.

Several investigators have tried to identify the cells which support the expression and replication of the virus. These studies have demonstrated HIV-1 products in mononucleated and multinucleated macrophages glial cells (Cheng-Mayer, C. et al., 1987, *Proc. Natl. Acad. Sci. U.S.A.,* 84:3526–3530; Epstein, L. G. et al., 1986, *Pediatrics,* 78:678–687; Gyorkey, F. et al., 1987, *J. Infect. Diseases,* 155:870–876; Koenig, S. et al., 1986, *Science,* 233:1089–1093; Stoler, M. H. et al., 1986, *JAMA,* 256:2360–2364; Vazeux, R. et al., 1987, *American J. Pathol.,* 126:403–410; Wiley, C. A. et al., 1986, *Proc. Natl. Acad. Sci. U.S.A.,* 83:7086–7093) endothelial cells and astrocytes (Epstein, L. G. et al., 1993, *Ann. Neurol.,* 33:429–436; Wiley, C. A. et al., 1986, *Proc. Natl. Acad. Sci. U.S.A.,* 83:7086–7093) microglial cells, but not in neurons (Savio, T. et al., 1993, *J. Neurosc. Res.,* 34:265–272; Sweetnam, P. M. et al., 1993, *Eur. J. Neurosc.,* 5:276–283). Furthermore, HIV-1 has been rescued from brain tissue and cerebrospinal fluid, but not from neurons (Pulliam, L. et al., 1993, *AIDS Res Hum Retroviruses,* 9:439–444). These findings appear rather paradoxical, considering the cognitive/motor dysfunctions, the dementing illness and the neuronal loss observed in many HIV-1 patients.

In absence of evidence for neuronal infectivity, several direct and indirect mechanisms have been proposed to account for the motor/cognitive disorders. a) It has been postulated that HIV-1 infection of monocytes or macrophages may activate inappropriate secretion of cytokines, such as interleukine-1 or tumor necrosis factor (TNF), that may impair neuronal and/or glial cell function or compromise the integrity of the blood-brain barrier (Wigdahl, B. et al., 1989, *AIDS Res. Hum. Retroviruses,* 5:369–374). b) Based on experimental observations showing that HIV-1 glycoprotein gp120 could inhibit the growth of neurons in the presence of neuroleukin, but not in the presence of nerve growth factor (Lee, M. R. et al., 1987, *Science,* 237:1047–1051), it has been suggested that the HIV-1 env protein may bind to and compete for neuroleukin receptors (Brenneman, D. E. et al., 1988, *Nature* (London), 335:639–642; Lee, M. R. et al., 1987, *Science,* 237:1047–1051). As a consequence, gp120 could directly interfere with neuronal cell function and/or cause neuronal cell death. c) Recent studies have shown that both native and recombinant gp120, added at very low concentrations to neuronal cultures produce a striking increase in free calcium within the cells and cause cell death within 24 hours, an effect which could be abolished by adding nimodipine (100 nM), the dihydropyridine calcium channel antagonist (Dreyer, E. B. et al., 1990, *Science,* 248:364–367), vasoactive intestinal peptide (Brenneman, D. E. et al., 1988, *Nature* (London), 335:639–642), anti-gpl 20 antibodies (Dreyer, E. B. et al., 1990, *Science,* 248:364–367) or NMDA antagonists (Brenneman, D. E. et al., 1988, *Nature* (London), 335:639–642; Lipton, S., 1991, *Brain Pathology,* 1:193–199). The neurotoxicity of gp120 may thus be conferred either through the NMDA receptor, via a second messenger, or directly by calcium channels (Levy, J. A. et al., 1985, *Lancet,* ii: 586–588; Lipton, S. A., 1992, *Trends Neurosci.,* 15: 76–80; Sweetnam, P. M. et al., 1993, *Eur. J. Neurosc.,* 5:276–283). Since gp120 shares certain sequence homology with vasoactive intestinal peptide it might also compete for the same binding sites and block this neurotransmission (Lee, M. R. et al., 1987, *Science,*

237:1047–1051). All these studies carried out in vitro have indicated possible mechanisms by which HIV infection could lead to AIDS dementia. However, many aspects related to AIDS neurophysiopathology are still obscure and could not be approached by in vitro techniques.

It would be highly desirable to be provided with transgenic mice carrying the HIV-1 env gene under the neuron specific promoter of human neurofilament light gene (NFL) (Julien, J. P. et al., 1987, *Genes & Development*, 1:1085–1095) to further define the role of gp120 in neurotoxicity. Such an animal model could provide some information on the effect(s) of gp120 when expressed in neuronal cells and should help identify the mechanism(s) involved in AIDS clinical syndrome and neuropathology.

It would be highly desirable to be provided with transgenic animals with the neuronal expression of gp120 and preliminary findings of the pathological evaluation.

SUMMARY OF THE INVENTION

One aim of the present invention is to provide a transgenic mice carrying the HIV-1 env gene under the neuron specific promoter of human neurofilament light gene (NFL) to further define the role of gp120.

Another aim of the present invention is to provide transgenic animals with the neuronal expression of gp120 and preliminary findings of the pathological evaluation.

In accordance with the present invention there is provided a transgenic non-human mammal, whose germ cells and somatic cells contain a recombinant env gene sequence which is operably linked to a promoter effective for the expression of the gene in the neuronal tissues of the mammal and effective for the simulation of neurological syndromes associated with HIV-1, the gene being introduced into the mammal, or an ancestor of the mammal, at an embryonic stage.

In accordance with the present invention the transgenic non-human mammal is such that transcription of the env gene may be under the control of a promoter sequence, such as a neuron specific promoter of human neurofilament light gene (NFL). The promoter can be synthetic or inducible.

In accordance with the present invention the transgenic non-human mammal can be a rodent, such as a mouse.

DETAILED DESCRIPTION OF THE INVENTION

1) Recombinant plasmids

Figure 1A:
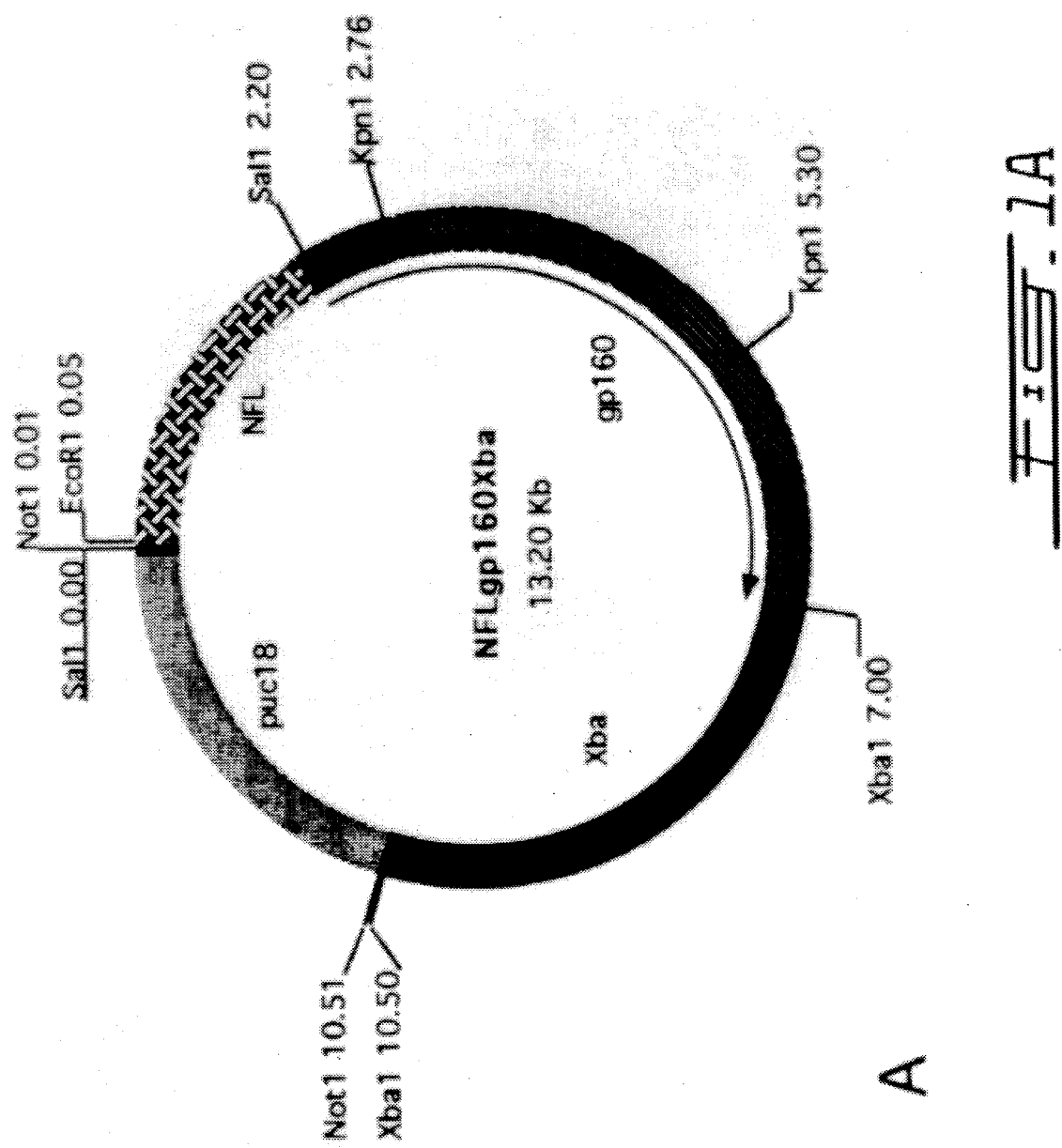
FIG. 1 illustrates the structure and restriction map of NFLgp160Xba and KS-StyT3 plasmids in accordance with the present invention.

The plasmid harboring the transgene NFLgp160 (FIG. 1A) was derived as follows: The pUC18 vector, harboring the 2.2 kb NFL promoter, was modified by introducing Not1 sites at the unique Kpn1 and EcoR1 sites. The 4.8 kb Sall-Xbal gp160 fragment of HIV-1 HXBc2 strain and the 3.5Skb Xba fragment of the NFL gene were introduced in the pUC18 at Sall and/or Xbal sites, as described in materials and methods. The 2.2 kb Sall segment containing the human NFL promoter was inserted in Sall site at the 5' end of the HIV-1 4.8 kb fragment. NFLgp160Xba transgene was deleted from the vector pUC18 by Not1 digestion before microinjection. The HXBc2 fragment expresses only rev and env proteins, the former being necessary for the transport of env mRNA from the nucleus to the cytoplasm. It also harbors the vpu and nef genes which are not expressed because of a premature stop codon in their respective sequences, the entire 3' LTR that provides the polyadenylation signal and 1.8 kb of cellular sequences with no function. The transgene was completed by fusing to the 3' end of the HIV-1 segment a 3.5 kb fragment corresponding to the Xba fragment of the human neurofilament gene. This segment was added because, according to J. P. Julien, it may contain positive regulatory elements which enhance the promoter activity.

For transient expression experiments in Cos-1 cells, the SV4 origin of replication was inserted in the pUC18 backbone of the construct. The KS-StyT3 construct (FIG. 1B) was derived to provide the probes for Southern, Northern and RNase protection analyses. KS-StyT3 plasmid was constructed by insertion of the 2.2 kb Hind III subfragment of HIV-1 env gene in Hind-III site of KS+ vector. This construct contains the 2.2kb Hind-III fragment of the env gene in Bluescript KS(+) vector (Stratagene). The env expressor plasmid, psvIIIexE7, and its non expressor derivative, psvIIIex ΔE7, were respectively used as positive and negative controls for in vitro expression experiments.

2) Cell cultures and transfections

The cell lines Cos-1, HeLa-CD4+ and HeLa-CD8+ used for transfection experiments were all maintained in Dulbecco modified Eagle medium (DMEM, Gibco/BRL) supplemented with 10% fetal bovine serum (Gibco/BRL.) and 0.1% gentamicin. HIV-1 infected and non-infected U937 were maintained in RPMI (Gibco/BRL) medium supplemented with 10% fetal bovine serum and 0.1% gentamicine. The transfections were performed by the standard calcium phosphate technique as described by (Shen, Y. M. et al., 1982, *Mol. Cell. Biol.*, 2:1145–1154) Fifteen micrograms of plasmid DNA, coprecipitated with calcium phosphate, were added for 12–16 hours to rapidly growing cells plated onto a 10 cm diameter plate containing 10 ml DMEM supplemented with 10% fetal bovine serum and 0.1% gentamicine. The cells were then rinsed with DMEM and incubated in fresh medium for 36 to 48 hours.

3) Immunoreactions a) Immunoprecipitation

The expression of gp160 precursor protein and its processed products, gp120 and gp41, was assessed by immunoprecipitation of Cos-1 cells transfected with the transgene construct. Two days after transfection with either NFLgp160, psvIIIexE7 (positive control) or psvIIIexΔE7 (negative control), Cos-1 cells were labelled with 100 μCi/ml of [$^{35}$S]

cysteine (600Ci/mmol) for 6 hours in cysteine-deficient DMEM. HIV-1 infected U937 cells were similarly labelled in cysteine deficient RPMI. The cells were washed and lysed in RIPA lysis buffer (20 mM Tris-HCl [pH 8.0], 1 mM EDTA, 120 mM NaCl, 1% NP40, 0.1% sodium dodecyl sulfate [SDS], 0.25% deoxycholate 0.2% phenyl-methylsulfonyl fluoride). The cell lysates were first clarified by centrifugation at 13000 rpm for one hour at 4° C. and the supernatant was reacted with normal serum for 2 hours at 4° C. The precipitates were pelleted by centrifugation at the same speed for 5 minutes; the supernatants were incubated at 4° C. overnight with the immunoserum of an HIV-1 infected patient. The immune complexes were precipitated for 2 hours at 4° C. with 50 μl of protein A-sepharose suspension. The precipitates were finally pelleted, washed 6 times with 1 ml of washing buffer (1% NP40, 120 mM NaCl, 20 mM Tris-HCl, pH 8.0) and resuspended in 50 μl of 2×SDS gel loading buffer (100 mM Tris.-HCl, pH 6.8, 200 mM dithiothreitol, 0.4% SDS, 0.2% bromophenol blue and 20% glycerol). They were boiled for 3 minutes and fractionnated on a 9% polyacrylamide/SDS gel. The gels were dried and exposed to radioautographic films for 24 to 48 hours.

b) Immunoperoxidase staining

For immunoperoxidase reaction, Cos-1, HeLa-CD4+ and HeLa-CD8+ cells were seeded on glass coverslips and transfected as described above. Forty-eight hours later, the transfected cells and the appropriate controls were rinsed with PBS, air dried, fixed in cold acetone for 10 minutes and reacted first with a normal serum for 20 minutes and then with mouse monoclonal antibodies (Dupont/NEN) directed against gp41 or gp120. The immunoreactivity was revealed according to the avidin/biotin/peroxidase method (ABC) using a biotinylated horse anti-mouse IgG and an ABC complex (Vectastain, Vector) with diaminobenzidine as chromogen. The cells were then rinsed with PBS, stained with hematoxylin for 10 seconds, washed in water, dehydrated in ethanol and coverslipped with DPX.

4) Microinjection of fertilized mouse eggs

The 10.5 kb fragment containing the transgene NFLgp160Xba was deleted from the plasmid using Not1 enzyme (FIG. 1A), purified with several phenol/chloroform extractions and ethanol precipitation and finally microinjected at 2 μg/ml into the male pronuclei of fertilized eggs. Microinjected eggs were transferred to the oviducts of pseudopregnant females. All the transgenic mice were developed and maintained in a pathogen-free facility.

5) DNA analysis of transgenic mice

The integration of the transgene into the mouse genome was assessed by Southern blot hybridization of genomic DNA. Tail samples of 3 week old mice were digested with proteinase K at 55° C. for at least 5 hours and the DNAs were purified by several phenol/chloroform/isoamyl alcohol and chloroform extractions followed by ethanol precipitation. Ten to 15 μg genomic DNAs were digested with either Sac-1 or EcoR-1 enzymes, fractionated on 1% agarose gels and transferred to nitrocellulose membrane (Schleicher & Schuell). The filters were prehybridized in 5× SSC (1 SSC is 150 mM NaCl and 5 mM $Na_3$ citrate [pH 7]) 1% SDS, 20 mM Tris (pH 7.5), 533 Denhart's solution (1× Denhart is 0.02% bovine serum albumine, 0.02% Ficoll™, 0.02% polyvinyl pyrolidone), 10% dextran sulfate and 100 μg/ml denatured salmon sperm DNA for at least 3 hr at 65° C. The DNA probe made of the env 2.2 kb HindIII subfragment labeled with $[a^{32}P]dCTP$ (3000Ci/mmol.) was denatured and added to the filter for an overnight hybridization at 65° C. The filter was then washed 10 min. at room temperature in 2×SSC, 1% SDS; 2×30 min. at 65° C. in 1×SSC and 1% SDS; 30 min. in 0.5×SSC,1% SDS; 1 min. in 0.2× SSC at room temperature. The filters were finally exposed to Kodak™ X-Omat AR and/or RP with an intensifying screen.

6) RNase protection assay

The RNAses protection experiments were carried out to detect the env mRNA expression and compare its level among different organs. Transgenic and control mice were sacrificed and tissue samples from the forebrain, cerebellum/brainstem, lung, liver, heart and kidney were removed and immediately frozen in liquid nitrogen. The RNAs were prepared by homogeneizing the different organs in 10 ml/g of a solution 3M LiCl/6M urea. The homogenates were kept on ice for 1 hour, sonicated for 1 minute and incubated at 0° C. overnight. The RNAs were harvested by centrifugation, rinsed with LiCl/urea solution, pelleted again and resupended in 10 mM Tris-HCl, pH 7.6, 1 mM EDTA, 0.5% SDS in volumes equivalent to 5 ml/gr original tissue. The RNAs were extracted with an equal volume of phenol/chloroform/isoamyl alcohol (24:24:1) followed with chloroform/isoamyl alcohol (24:1) and finally precipitated in 2 volumes ethanol, 1/10 volume 3M NaOAc at −20° C. The purified RNAs were again pelleted, redissolved in sterile water and kept at −80° C. until use. As positive control, RNAs from HIV-1 infected U937 monocytic cells were prepared in the same conditions. For RNases protection reactions, RNA samples (25 μg) were redissolved in 30 μl of hybridization buffer containing $2.5 \times 10^5$ cpm of an antisens env RNA probe labeled with $[a^{32}P]UTP$ (3000 Ci/mmol). This probe was transcribed from StyI linearized KS-StyT3 plasmid using T3 polymerase; it spanned 92 nucleotides specific to gp160 transcripts and 73 nucleotides belonging to the KS(+) plasmid. As a standard for these hybridization reactions, we used a 292 nucleotides antisens RNA probe specific to the ubiquitus L32 riboprotein mRNA (Guy, C. T. et al., 1992, *Mol. Cell. Biol.*, 12:954–961) and labeled with $[^{35}S]UTP$ (3000 Ci/mmol). The hybridization products were digested with 0.1 μg and 5 μg of RNases T1 and A (BRL), respectively, and fractionnated on 8% polyacrylamide/urea gels. The gels were dried and exposed to X-Omat AR™ films with intensifying screens for 2 to 8 days.

7) In vitro expression of the transgene

The expression of the env proteins in the nervous tissues of transgenic mice was investigated by immunohistochemistry, using monoclonal antibodies against gp41 and gp120 or the serum from an HIV-1 infected patient. Transgenic and control mice were anesthetized with an overdose of pentobarbital (Somnotol, 70 mg/kg, i.p.), and perfused transcardially with 0.01M PBS, pH 7.4 followed by 4% paraformaldehyde in 0.1M phosphate buffer, pH 7.4. The brain and spinal cord were removed, further fixed by immersion in the same fixative and then cut into 40 μm thick sections with a vibratome. The sections were rinsed extensively, preincubated with 10% normal goat serum for 2 hours and incubated overnight at room temperature with the primary antibodies. This was followed by PBS washings and immunoreactivity detection according to the ABC method (Vectastain™ Vector). The sections were mounted on slides, air dried at 37° C. overnight, dehydrated with ethanol and coverslipped with DPX mountant. The stereotaxic atlas for the rat and the atlas of the mouse brain and spinal cord were used as anatomical references.

Figure 2:
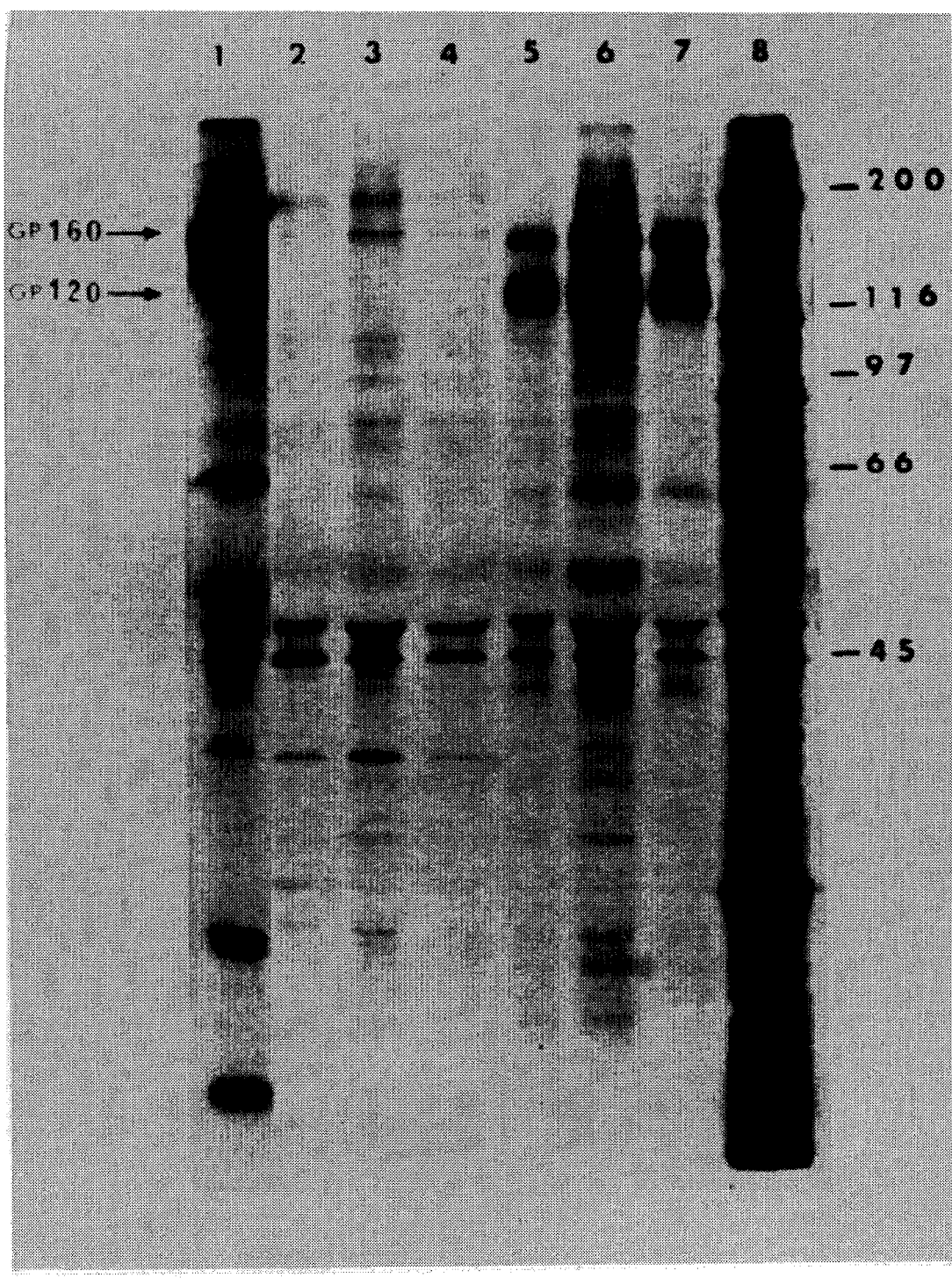
FIG. 2 illustrates the in vitro expression of the transgene, where Cos-1 cells were transfected with NFLgp160Xba, env expressor psvIIIexE7 and its negative derivative psvIIIexΔE7.
Figure 3A:
FIG. 3 illustrates the functional properties of the transgenic env proteins in accordance with the present invention.
Figure 3B:
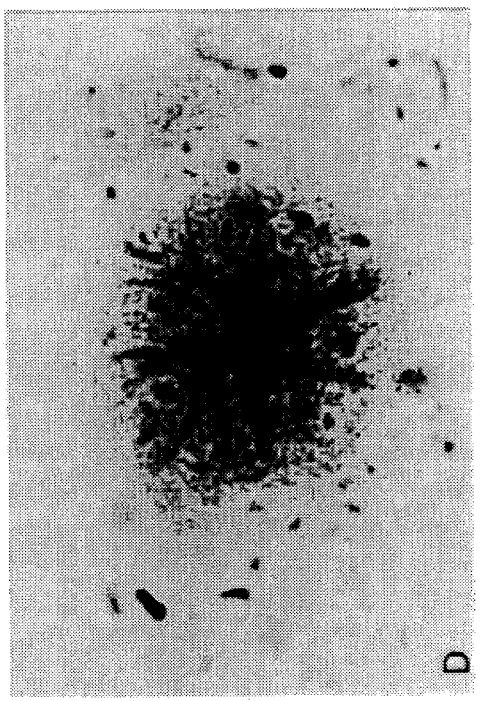
Figure 3C:
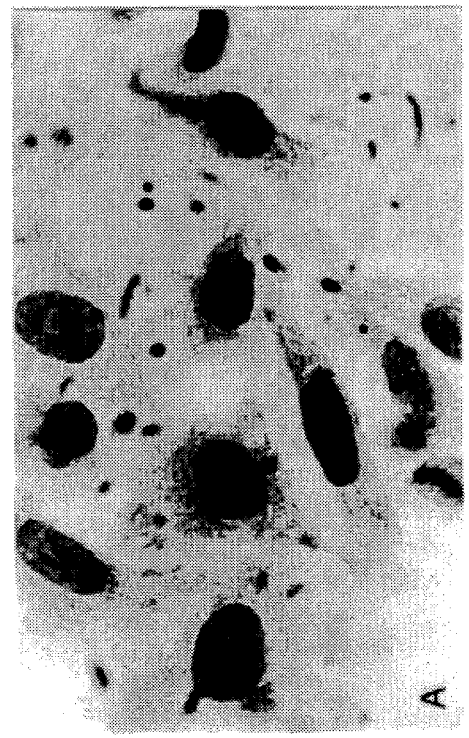
Figure 3D:
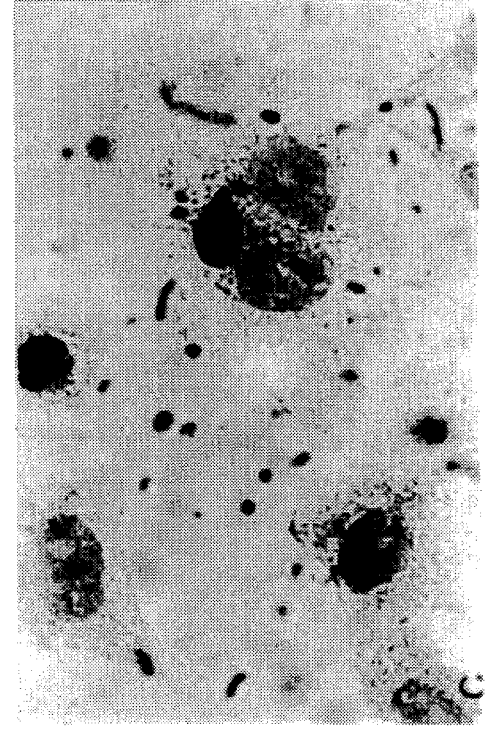

Before using the NFLgp160Xba transgene to develop transgenic animals we carried out transient expression experiments to determine if the HIV-1 env products, under the control of the heterologous NFL promoter, were expressed and processed correctly. Cos-1 cells were transfected either with NFLgp160Xba, the env expressor psvIIIexE7 or its negative derivative psvIIIexΔE7, and metabolically labeled with [$^{35}$S]cysteine. The radiolabeled lysates of the transfected cells and appropriate controls including non infected and HIV-1 infected U937 cells were immuno-precipitated with total immune sera from normal and HIV-1 infected individuals. The autoradiogram in FIG. 2 (lanes 1 to 8) illustrates the results of these experiments. Cos-1 cells were transfected with NFLgp160Xba (that has been modified by addition of a 450 bp fragment harboring SV40 origin of replication), env expressor psvIIIexE7 and its negative derivative psvIIIexΔE7. The immunoprecipitation reaction was performed using normal or HIV-1 infected patients immunoserum. The immunoprecipitates of HIV-1 infected controls and transfected Cos-1 cells are shown in the autoradiogram. Lane 1: HIV-1 infected U937 cells; lane 2: non transfected Cos-1 cells; lane 3: psvIIIexΔE7 transfected Cos-1 cells; Lanes 4: NFLgp160Xba-cos immunoprecipitated with human normal serum; lanes 5 and 6: NFLgp160Xba-cos transfected cells (15 and 30 mg, respectively) immunoprecipitated with human anti-HIV-1 serum. Lanes 7 and 8: psvIIIexE7 transfected cells immunoprecipitated with human anti-HIV-1 and normal sera, respectively. Arrows indicate the position of the gp160 and gp120. HIV-1 infected U937 cell lysates treated with the immunoreactive serum showed the signals corresponding to gp120 and its precursor gp160 (lane 1). Similar signals were obtained with lysates of Cos-1 cells transfected with 15 and 30 µg of NFLgp160Xba plasmid DNA (FIG. 2, lanes 5 and 6 respectively) or with the HIV-1 env expressor psvIIIexE7 (FIG. 2, lane 7). The control reactions which included lysates of non transfected Cos-1 cells treated with normal or HIV-1 immune sera (FIG. 2, lanes 2 and 3, respectively), Cos-1 cells transfected with the psvIIIexΔE7 plasmid (FIG. 2, lane 4), as well as lysates of Cos-1 cells transfected with the env expressor psvIIIexE7, but immunoprecipitated with normal serum (FIG. 2, lane 8), were all negative for the signals corresponding to gp120 and gp160. The gp41 protein, which is present in equimolar ratio to gp120 in the immunoprecipitates of positive samples, was less clearly visualized on the autoradiograms. Since the NFLgp160Xba transgene was found to express the gp160 protein and its subunits gp120 and gp41, it was important to determine if the env moiety encoded by this recombinant construct had retained the biological property to induce syncitia in CD4+ cells. Immunostaining of NFLgp160Xba transfected HeLa-CD4+ and HeLa-CD8+ cells, with monoclonal antibodies against gp41 or gp120 showed that both types of cells expressed the viral envelope proteins (FIGS. 3B and 3D). The CD4+ and CD8+ HeLa cells transfected with the transgenic construct were immunoreacted with either normal or monoclonal antibodies against gp120 and gp41 using Avidin/biotin/peroxidase technique and examined for syncitia formation. A: CD8+ HeLa cells with normal serum; B: CD8+ HeLa cells treated with anti-gp120 or anti-gp41; C: HeLa CD4+ cells immunoreacted with normal serum; D: HeLa CD4+ cells treated with anti-gp120 or gp41. Syncitia are observed only in CD4+ cells expressing the env proteins (C and D). Magnification ×2600. Although present on the cell surface and all over the cytoplasm, the protein was mostly concentrated in areas corresponding to the rough endoplasmic reticulum/Golgi compartments, as already reported (Stein, B. S. et al., 1990, J Biol Chem, 265:2640–2649). No immunostaining was found in cells reacted with normal serum (FIGS. 3A and 3C). As anticipated, several multinucleated cells were observed in HeLa-CD4+ (FIGS. 3C and 3D), but not in HeLa-CD8+ transfected cells (FIGS. 3A and 3B). In these syncitia, the nuclei were often forming a ring around the immunostained area. These findings confirmed that the NFLapl60Xba construct was correctly expressing the HIV-1 envelope components and clearly indicated that gp120, like the native protein in HIV-1 infected cells, was capable of inducing syncitia formation.

8) Transgenic mice

The integration of the transgene in the mouse genome was determined by Southern blot hybridization of genomic DNA extracted from mice tails. Out of 25 animals tested, 3 were found to carry 1 to 30 full length copies of the transgene per haploid genome. These 3 founders, 844, 852 and 854, were maintained in a pathogen-free facility and, for 11 months now, have remained apparently healthy. They all reproduced normally and transmitted the transgene in a mendelian fashion, except for female 852 which was found less fertile. Heterozygous colonies of transgenic mice have been developed from founders 844 and 854 and a homozygous line has already been established from founder 854. Because of its lower fertility, founder 852 had, from several matings, three F1 transgenic offsprings that are still used as progenitors to develop a colony.

9) Expression pattern of the env mRNA in the transgenic mice

Tissue specific expression of the NFL driven env gene in transgenic animals was analyzed by RNases protection assay on RNAs extracted from the targeted nervous tissues, (forebrain and cerebellum/brainstem), as well as from non targeted organs such as heart, liver, kidney and lung, of three months old mice derived from 844 and 854 founders. The reaction specificity was controlled with RNAs purified from the same organs of non transgenic littermates and from HIV-1 infected U937 =cells. Equal amounts of sample RNAs were simultaneously hybridized to [a$^{32}$P]UTP labeled antisens RNA probe specific to env transcripts and [$^{35}$S]UTP labeled antisens probe specific to L32 ribosomal protein mRNA. As illustrated on the autoradiogram in FIG. 4 (lanes 5 to 23), a signal with similar intensity and corresponding to the protected segment of the L32 probe was observed in all the tested RNA samples; this indicated that the hybridization reactions contained approximately equivalent amounts of RNA. RNAs isolated from different tissues of normal and transgenic mice 844 and 854 and HIV-1 infected U937 cells were hybridized to gp160 and L32 ribosomal gene specific probes. The env $^{32}$P-labeled antisens RNA was transcribed from StyI digested KS-StyIT3 plasmid and protected 92 nucleotides of gp160 mRNA. The $^{35}$S-labeled probe for internal control L32 ribosomal gene was transcribed from XbaI linearized rpL3227.3.7 plasmid and protected 278 nucleotides of L32 mRNAs. The RNase protected products were analyzed on 8% polyacrylamide/urea gels and distributed as follows: RNAs from forebrain, cerebellum/brainstem, heart, liver, lung and kidney of normal mouse are respectively in lanes 5 to 11; in the-same order, the RNA samples from the same tissues of transgenic mice 844 are in lanes 12 to 17 and from mice 854 in lanes 18 to 23. RNA sample from HIV-1 infected cells is in lane 25.

Figure 4:
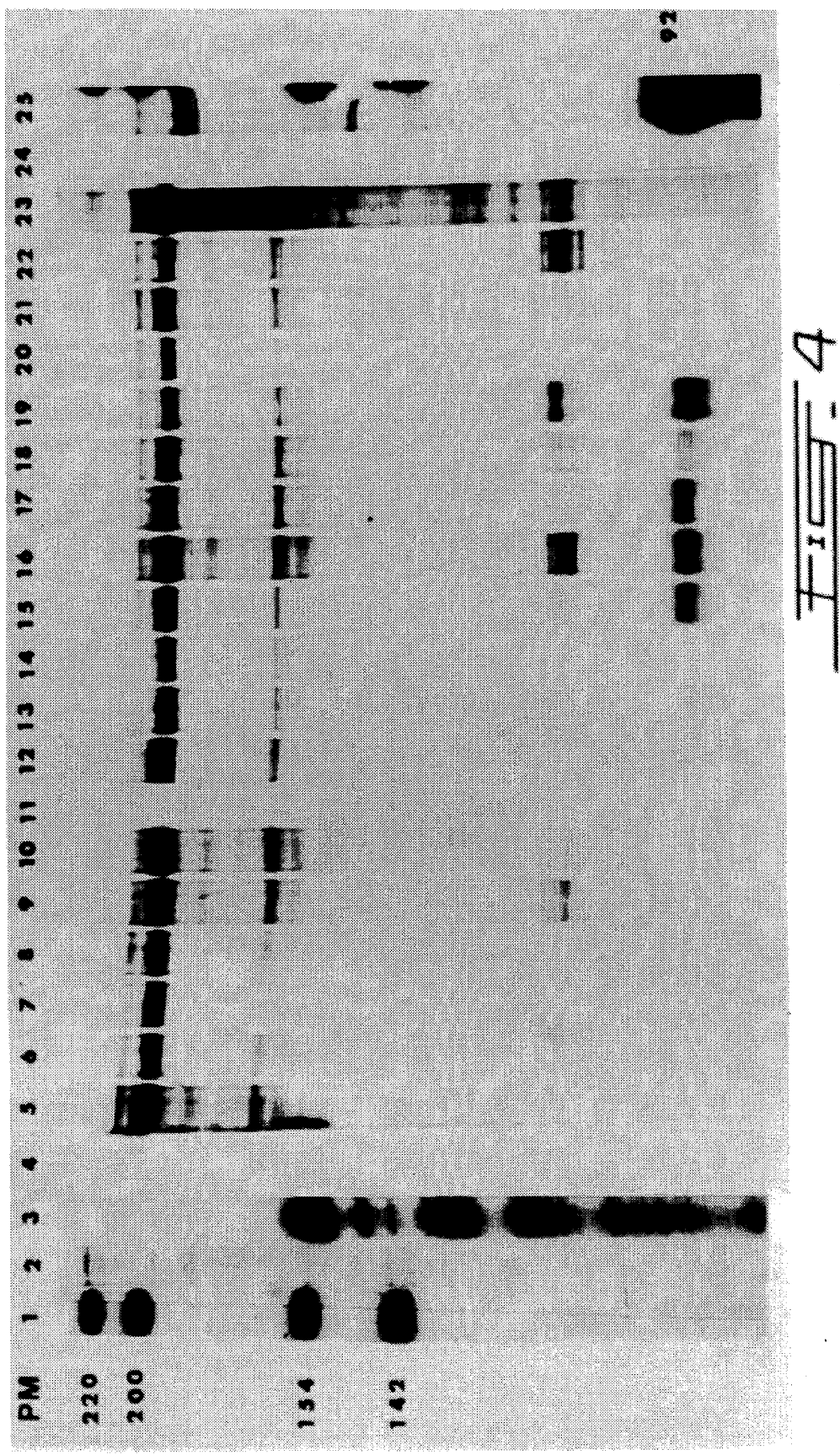
FIG. 4 is the RNases protection analysis of the env mRNA expression in transgenic tissues.

The hybridization of test samples with the probe specific for the gp160•transcripts led to the following findings.

i) the RNAs from infected cells exhibited a protected fragment of 92 nucleotides (FIG. 4, lane 25).

ii) The forebrain, cerebellum/brainstem, heart, liver, lung and kidney of the normal mouse (FIG. 4, lanes 5 to 10, respectively) were all negative.

iii) With the RNAs of the 844 transgenic mice, the probe specific for gp160 transcripts protected the anticipated 92 nucleotides segment in forebrain and cerebellum/brainstem (FIG. 4, lanes 12 and 13) and unexpectedly, in non targeted organs such as heart, liver, lung and kidney (lanes 14 to 17, respectively). Curiously, the level of env mRNAs expression in the CNS tissues appeared lower than that of the ectopic organs.

iv) In contrast, among all the tissues tested in heterozygous or homozygous mice of line 854, only the forebrain and cerebellum/brainstem exhibited the protected fragment (FIG. 4, lanes 18 and 19, respectively). No signficant signal was observed in the other tissues (FIG. 4, lanes 20 to 23). Overall, these results clearly indicated that the transgene was transcribed in the CNS of both investigated lines. In addition, they showed in both transgenic mice a higher level of env mRNA expression in the cerebellum/brainstem than in the forebrain.

10) Distribution of Env proteins in the CNS of transgenic mice

Figure 5A:
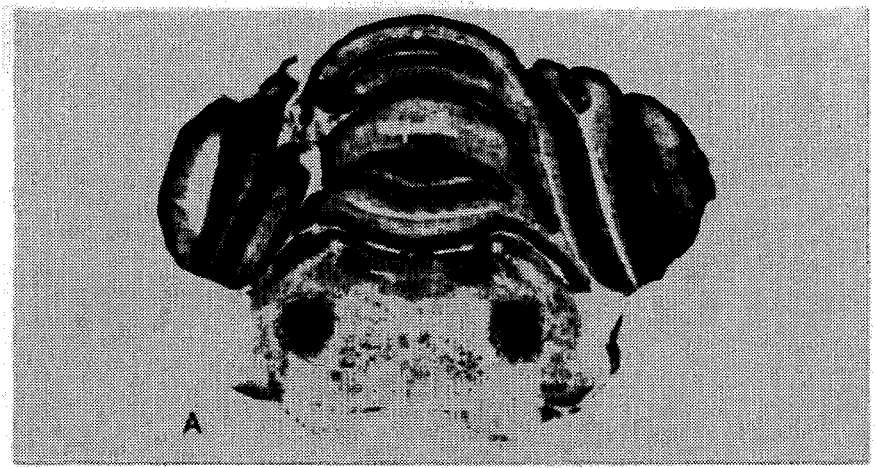
FIG. 5 shows the immunodetection of HIV-1 env proteins in CNS sections of transgenic mice 844 and 854 with human anti-HIV-1 serum.
Figure 5B:
Figure 5C:

Immunohistochemistry with a HIV-1 infected human immunoserum and monoclonal antibodies against gp41 and gp120 was performed on serial sections of the brain and spinal cord from three month-old transgenic (lines 844 and 854) and control mice. The forebrain (telencephalon and diencephalon) of both types of transgenic mice was essentially immunonegative, with the exception of the lateral hypothalamus (LH) in line 844, which displayed some immunostained cell bodies with the HIV-1 immunoserum. The cerebellum was also completely immunonegative. In contrast, several nuclei of the brainstem and spinal cord exhibited immunoreactive perikarya (Table 1 and FIG. 5).

Their distribution was consistent among transgenic mice of both lines and with all three antibodies, although the HIV-1 human immunoserum was the most sensitive, producing a more intense staining which indicated some brain areas immunonegative with one or both of the other antibodies. The motoneurons of cranial nerve nuclei (3, 4, 5, 7, 12) and spinal cord (FIGS. 5A, 5B and 5C) were the most prominent in terms of number of labeled neurons and staining intensity, the immunoreactivity extending distally into the dendrites. A) Immunolabeling of motor trigeminal neurons (Mo5); B) Immunolabelling of the motor facial neurons (7); C) Immunostaining of neurons in the anterior gray horns of the spinal cord. Magnification: A ×15, B ×15, C ×40. Lower numbers of labeled neurons were observed in the mesencephalic, pontine and medullar reticular formation (DDMe, PnO/PnC, MdV/Gi, LRt), the red nucleus (R), superior colliculus (SC), lateral and superior vestibular nuclei (LVe, SuVe) and dorsal root ganglia (DRG). Thus, most brain regions which were shown in other studies to display perikaryal NFL immunoreactivity in normal adult mouse were also immunopositive for env proteins in NFLgp160Xba transgenic mice, with the notable exception of the cerebral and cerebellar cortices. However, a few brain areas immunopositive in one or both transgenic mouse lines were found unlabeled for NFL in normal mice: LH, LRt and layers 4–8 of spinal cord. These areas were nevertheless immunopositive for NFL during postnatal development, in normal mice and in adult mice transgenic for human NFL.

TABLE 1

CNS distribution of neuronal perikarya immuno-reactive with HIV-1 infected human serum, or with anti-gp41 or anti-gp 120 antibodies in two lines of NFLgp160 transgenic mouse

|  |  | LINE 844 | | | LINE 854 | | |
|---|---|---|---|---|---|---|---|
|  |  | Human serum | gp41 | gp120 | Human serum | gp41 | gp120 |
| HYPOTHALAMUS | LM | − | − | − | ND | − | − |
|  | LH | + | − | − | ND | − | − |
| MESENCEPHALON | R | + | − | − | + | + | − |
|  | SNR | − | − | − | − | − | − |
|  | 3 | ++ | − | − | ++ | + | − |
|  | SC | + | − | − | + | + | − |
|  | IC | ND | ND | ND | − | − | − |
|  | 4 | ++ | − | − | ++ | + | − |
|  | DpMe | + | − | − | + | + | − |
|  | PCom | + | − | − | ND | − | − |
| PONS | PnO/PnC | + | − | + | ++ | + | − |
|  | Pr5 | − | − | − | − | − | − |
|  | Mo5 | +++ | +++ | ++ | ++ | ++ | ++ |
|  | Sp5 | + | − | − | + | + | + |
|  | Acs5 | ++ | + | + | + | + | + |
|  | Me5 | + | + | + | ++ | ++ | + |
|  | 6 | − | − | − | − | − | − |
|  | 7 | ++ | ++ | + | ++ | + | + |
|  | Acs7 | ++ | + | + | ++ | + | − |
|  | LVe | + | − | + | + | + | + |
|  | SuVe | + | − | + | + | + | ND |
|  | SubCA | − | − | − | − | − | ND |
|  | VLL | − | − | − | + | ND | ND |
|  | PL | − | − | − | + | ND | ND |
| MEDULLA | 10 | − | − | − | − | − | − |
|  | 12 | ++ | ++ | + | + | + | + |
|  | Amb | + | − | − | + | − | − |
|  | MdV/Gi | + | + | + | + | − | − |
|  | LRt | + | ++ | + | ++ | − | − |
| CEREBELLUM | Purkinje cell layer | − | − | − | − | − | − |
|  | Deep nuclei | − | − | − | − | − | − |
| SPINAL CORD | DRG | + | ND | ND | ND | ND | ND |
|  | Layers 4–8 | − | − | − | ND | + | ND |
|  | Motoneurons | ++ | − | ND | + | ND | ND |

CNS distribution of neuronal perikarya immunoreactive with HIV-1 infected human serum, or with antibodies against gp41 or gp120 in two lines of NFLgp160 transgenic mouse.

Semi-quantitative estimates of the number of immunoreactive neurons rated on a scale from – (absent) to +++ (virtually every neuron); ND, (not determined).

Data were collected from transverse 40 μm-thick sections taken every 200 μm through the whole brain and from sections of the cervical spinal cord and dorsal root ganglia. Neuroanatomical abbreviations: 3, Oculomotor nucleus; 4, Trochlear nucleus; 6, Abducens nucleus; 7, Facial nucleus; 10, Dorsal motor nucleus of vagus; 12, Hypoglossal nucleus; Acs5, Accessory trigeminal nucleus; Acs7, Accessory facial nucleus; Amb, Ambiguus nucleus; DpMe, Deep mesencephalic nucleus; DRG, Dorsal root ganglia; Gi, Gigantocellular reticular nucleus; IC, Inferior colliculus; LH, Lateral hypothalamic area; LM, Lateral mammillary nucleus; LRt, Lateral reticular nucleus; LVe, Lateral vestibular nucleus; MdV, Medullary reticular nucleus, ventral part; Me5, Mesencephalic trigeminal nucleus; Mo5, Motor trigeminal nucleus; PCom, Nucleus of the posterior commissure; PL, Paralemniscal nucleus; PnC, Pontine reticular nucleus, caudal part; PnO, Pontine reticular nucleus, oral part; Pr5, Principal sensory trigeminal nucleus; R, Red nucleus; SC, Superior colliculus; SNR, Substantia nigra, reticular part; Sp5, Spinal trigeminal tract nucleus; SubCA, Subcoeruleus nucleus, alpha part; SuVe, Superior vestibular nucleus; VLL, Ventral nucleus of tha lateral lemniscus.

11) Neuropathological evaluation

The CNS of transgenic and control mice was also fixed in 10% formaldehyde and embedded in paraffin blocks for serial 5 μm-thick sectionning. The sections were stained with hematoxylin-phloxin-safran (HPS). Selected sections were further stained with modified Bielchowsky™, Luxolcresyl™ violet and Holzer™ stains. Preliminary immunohistochemical exploration for GFAP and the phosphorylated neurofilament triplet was done with the ABC method.

Figure 6A:
FIG. 6 illustrates the neuropathological changes associated with the neuronal env expression.

Preliminary observations with anti-HIV-1 immunostaining in the CNS of three month old transgenic 844 and 854 mice showed a similar topographic distribution of the env protein in sections from paraffinembedded brain although these antibodies did not react as strongly as in non embedded tissue. Most immunostained cells appeared normal in shape. The reaction was confined to the perikaryal area with a variable extension into the dendrites (FIG. 6A). A) Neuron of the reticular formation of the medulla. Intense immunostaining in perikaryon with extension in the dendritic tree. B) Immunostaining of numerous neurons in the 5th motor nucleus. Elongated (arrow) or spherical (arrowhead) neuritic swellings present in or around the nucleus. C) Gracilis nucleus with numerous immunostained neuritic swellings of variable size. D) Immunostained segment of one axon with row of swellings in the dorsal horn of the spinal cord. Magnification: A×800, B×320, C×800, D×1280. Initial segments of axons were occasionally positive. The modified Bielschowsky™ and the antibodies against the phosphorylated neurofilament triplet remained negative in the perikarya of gp160 positive nuclei of brainstem and spinal cord anterior gray horn. However these two stains showed the expected positivity in axons of various tracts and nerve roots.

Figure 6B:
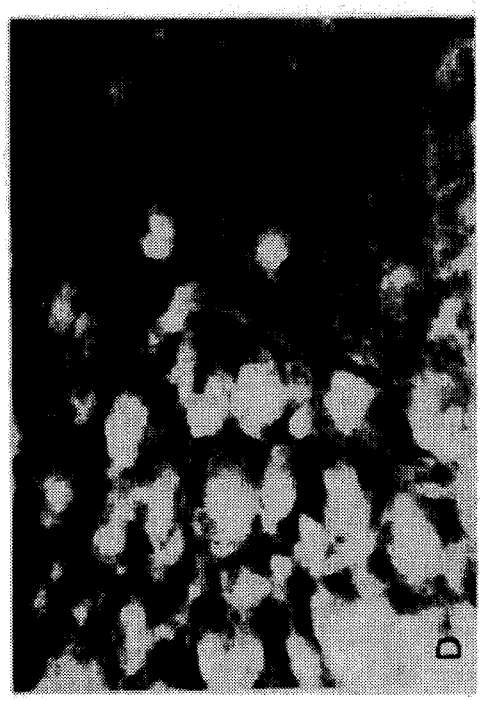
Figure 6C:
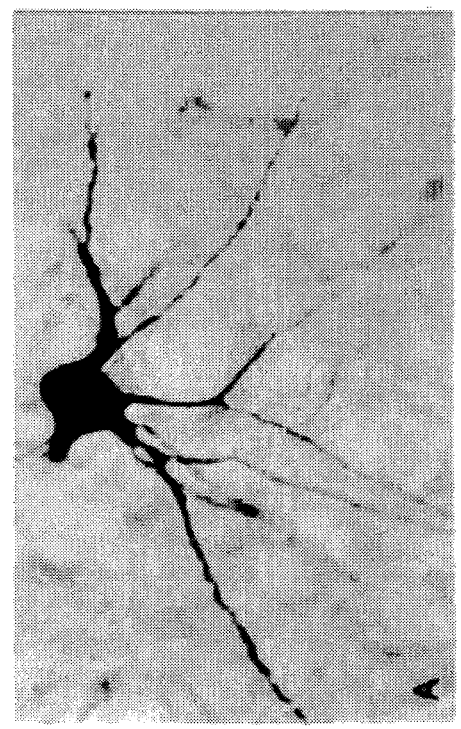
Figure 6D:
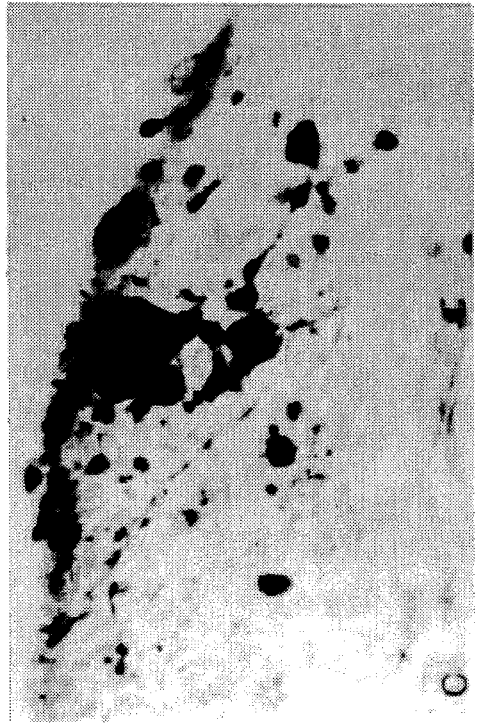

With the anti-HIV-1 antibodies, particularly in non-embedded vibratome sections but also in paraffinembedded sections, numerous small abnormal dendritic swellings were found in and around the most intensely stained motor nuclei such as the motor trigeminal (Mo5) and the facial (7) nuclei (FIG. 6B); they were also present in anterior gray horn of the spinal cord. Interestingly, these dendritic swellings were not stained with antibodies against phosphorylated neurofilament triplet or with the modified Bielschowsky method, which suggests that the neurofilaments were not involved in these changes. In addition, HIV-1 immunoreactive axonal swellings were also observed in a region corresponding to nucleus gracilis and to the gracilis and cuneate fascicles in the medulla and spinal cord (FIG. 6C). Similar swellings were occasionally found in the same regions of the CNS in control mice, but they were much more numerous and larger in transgenic animals. These were stained by the antibodies against the phosphorylated neurofilament triplet and the modified Bielschowsky™ stain, but this reaction was variable in intensity. Finally some axonal swellings were found in other areas of the medulla and spinal cord (FIG. 6D).

The glial fibrillary acidic protein (GFAP) reaction suggested early reactive astrocytosis in several areas of the CNS. Quantitative analysis to better evaluate it are in progress. The hematoxylin/phloxin/safran (HPS) did not show any sign of inflammatory reaction, migration disorder, or any developmental or acquired changes. The HPS was also used for evaluation of the thoracic and abdominal organs: no inflammation or cytological changes were observed.

Discussion

The results described in accordance with the present invention clearly show that NFLgp160Xba transgenic mice express the HIV-1 env proteins in their CNS. In this transgene the env protein expression was driven by the neuron specific promoter of the human NFL. Analysis of the expression products of NFLgp160Xba construct in Cos-1 and HeLa-CD4+ cells has shown that the recombinant proteins were very similar to the native moieties with respect to their processing and biological function.

In both 844 and 854 lines, env transcripts have been detected in cerebellum/brainstem and forebrain, although, in the latter region, the signal was always lower. As anticipated with the NFL promoter, the transgene expression was restricted to the nervous tissue in line 854: no transcriptional activity was detected in ectopic organs. In mice 844, however, RNAses protection experiments demonstrated the presence of env mRNAs not only in CNS but also in liver, kidney, heart and lung. Such ectopic expression could be explained by integration site effects as already reported for various genes in different transgenic animals. The expression of the env protein or its localization within these ectopic tissues has not yet been determined, but does not appear to have any effect according to the aspect of these tissues after HPS staining.

Notwithstanding these differences in mRNA expression, the expression and distribution of the env proteins in the CNS were identical for both 844 and 854 mice. They represent the first animal model displaying neuronal expression of HIV-1 env proteins. In the transgenic mice developped by Toggas et al. (1994, Nature, 367:188–193), in which the expression of gp120 was under the control of the GFAP promoter, the env protein was not detected despite the presence of high level of mRNA. As already mentioned, the immunoreactive structures in NFLgp160Xba mice were all localized in the brainstem and spinal cord. Most of the labeled nuclei displayed also perikaryal NFL immunoreactivity in normal adult or developing mice. The NFL promoter has thus responded as expected for these areas. Additional structures like LH, LRt and layers 4–8 of spinal cord, where the NFL protein is normally not detected in perikarya, displayed env positive neuronal cell bodies. Interestingly, these same areas were found immunoreactive for the NFL protein in transgenic animals carrying the human neurofilament light gene. It thus appears that env proteins were detected in neurons that express the highest levels of NFL. Surprisingly, no significant env immunopositivity was observed in cerebral cortex although NFL protein is normally present in perikarya in layers II/III and V of the parietal cortex. This apparent absence of env protein could be due to the low level of expression of the transgene in the forebrain of both transgenic mice, as demonstrated by the RNAses protection assay. It could also be the effect of a neuronal loss due to neurotoxic properties of gpl20. The loss of certain neuronal subpopulations has been well documented in HIV-1 infected patients; it was also reported in GFAP-gpl20 transgenic mice by Toggas et al., (1994, *Nature,* 367:188–193). If such a loss had occured in NFLgpl60Xba transgenic mice, one would predicts that NFL immunoreactivity in parietal cortex should also be reduced. To test this possibility immunostaining of alternate series of vibratome sections was performed with anti-NFL and anti-HIV-1 antibodies. These experiments showed a normal distribution of NFL immunoreactive cell bodies in cerebral cortex of the transgenic mice thus indicating that the absence of HIV-1 immunoreactivity in layers II/III and V in the parietal cortex was not related to neuronal loss in these structures.

Neuropathological evaluation of the two transgenic lines demonstrated cellular alterations manifested by two types of neuritic swellings. In brain regions with high HIV-1 env protein expression i.e. brainstem motor nuclei and the anterior gray horns of the spinal cord, such morphological anomalies were observed in the dendritic trees, sometimes quite distally. The negative reaction of the small neuritic swellings in the motor nuclei and anterior gray horns with the modified Bielschowski and with antibodies directed against the phosphorylated neurofilament triplet suggests that this anomaly did not involve neurofilaments. However, the involvement of the neurocytoskeleton should not be totally excluded until analyses of ageing animals are completed. In addition, early reactive astrocytosis, as demonstrated by the GFAP staining in several CNS structures, suggests that there may be a neuronal loss in these young mice. A second type of neuritic swelling was found in the gracilis nuclei and cuneate fascicles. These large, pleomorphic structures seem to represent an amplification of a normal physiological process since similar, but fewer and smaller spheroids were also present in normal mice. Their immunoreactivity with anti-HIV1 antibodies shows that the env protein was axonally transported. In conclusion, the expression of the env proteins in the CNS of these transgenic mice has produced moderate changes of the dendritic trees that could represent a first phenotypic manifestation of neuronal dysfunction. The limited effects we have detected could be related to a low level of gpl20 in neurons. Indeed, Toggas et al. (1994, *Nature,* 367:188–193) have reported that the severity of neuropathological changes in GFAP-gpl20 transgenic mice correlated with the level of gpl20 mRNA expression. The mild pathological changes we have observed could also be due to the relatively young age at which these animals have been analyzed.

The preliminary neurocytological anomalies observed in the dendritic trees of motor neurons in our transgenic mice reproduced changes present in the cerebral cortex in human AIDS (Masliah, E. et al., 1992, *Lab.Investigation,* 66:285–291). In humans, the possibility that these changes could have been caused by an inflammatory process rather than by the viral infection itself cannot be excluded. In NFLgpl60Xba mice, so far, there was no inflammatory process and hence, the observed changes could be a direct effect of env protein expression. Extensive analysis of these transgenic mice by electron and confocal microscopy is in progress and might yield some clues on the role and mechanisms of HIV-1 env neuronal toxicity in AIDS infected individuals.

2Further studies using offsprings obtained from matings of different transgenic lines will help determine the effects of higher levels of gpl20 on CNS morphology. In addition, the neuronal expression of env proteins at levels detectable by immunocytochemistry in several CNS regions of these animals provides useful models for studies of the neuropathological effects of gpl20 during embryonic development and ageing.

Uses of the transgenic mice

The transgenic mice of the present invention can be used for the study of neurobiology and to understand the function of neuronal cells.

The transgenic mice of the present invention can be used for the study of the mechanism of the neurotoxicity induced by gpl60.

The transgenic mice of the present invention can be used to test pharmaceutical compounds for used as antagonist against the neurotoxicity induced by gpl60 or for the treatment of the neuronal syndrome of HIV-1 infections.

The transgenic mice of the present invention can be combined to other transgenic mice which are carrying other genes of HIV for the study of the pathogenesis of this virus and the testing of pharmaceutical compounds effective against the pathogenesis.

While the invention has been described in connection with specific embodiments thereof, it will be understood that it is capable of further modifications and this application is intended to cover any variations, uses, or adaptations of the invention following, in general, the principles of the invention and including such departures from the present disclosure as come within known or customary practice within the art to which the invention pertains and as may be applied to the essential features hereinbefore set forth, and as follows in the scope of the appended claims.

Other embodiments are within the following claims. For example, any species of transgenic animal can be employed. In some circumstances, for instance, it may be desirable to use a species, e.g., such as the rhesus monkey, which is evolutionary closer to human.

We claim:

1. A transgenic mouse whose germ cells and somatic cells contain a recombinant HIV-1 env gene sequence which is operably linked to a neuron specific promoter of human neurofilament light gene (NFL) effective for the expression of said HIV-1 env gene sequence in the neuronal tissues of said mouse and wherein expression of said env gene produces neuropathological changes associated with HIV-1 wherein said neuropathological changes are selected from the group consisting of HIV-1 immunoreactive axonal swelling, dendritic swelling, and astrocytosis in the central nervous system; wherein said env gene is introduced into said mouse or an ancestor of said mouse at an embryonic stage.

* * * * *